United States Patent [19]

Van Nordstrand

[11] Patent Number: 4,547,472

[45] Date of Patent: Oct. 15, 1985

[54] METHOD OF ADDING AN ALKALINE EARTH METAL TO A ZEOLITIC CATALYST

[75] Inventor: Robert A. Van Nordstrand, San Rafael, Calif.

[73] Assignee: Chevron Research Company, San Francisco, Calif.

[21] Appl. No.: 614,889

[22] Filed: May 29, 1984

[51] Int. Cl.[4] ............................................. B01J 29/12
[52] U.S. Cl. ........................................ 502/66; 502/74
[58] Field of Search ............................ 502/66, 74, 79; 423/112, 328

[56] References Cited

U.S. PATENT DOCUMENTS

| 3,375,065 | 3/1968 | McDaniel et al. | 502/79 X |
| 3,794,600 | 2/1974 | Schutt | 423/112 X |
| 4,435,283 | 3/1984 | Buss et al. | 208/138 |

Primary Examiner—Carl F. Dees
Attorney, Agent, or Firm—S. R. LaPaglia; W. K. Turner; E. A. Schaal

[57] ABSTRACT

A method is disclosed for adding barium to a large-pore zeolite. The large-pore zeolite is ion exchanged with a barium nitrate solution at a pH of from 8 to 11; the ion exchanged large-pore zeolite is dried; the dried large-pore zeolite is calcined at a temperature of from 500° C. to 700° C.; and then the calcined large-pore zeolite is ion exchanged again with the barium nitrate solution at a pH of from 8 to 11.

8 Claims, No Drawings

METHOD OF ADDING AN ALKALINE EARTH METAL TO A ZEOLITIC CATALYST

BACKGROUND OF THE INVENTION

The present invention concerns a new method of adding an alkaline earth metal to a large-pore zeolite. This method completely eliminates the acid function from the zeolite and inserts the alkaline earth metal into as many exchange sites as possible. The resulting catalyst has a high selectivity for dehydrocyclization.

Catalytic reforming is well known in the petroleum industry. It involves treating naphtha fractions to improve the octane rating by producing aromatics. The hydrocarbon reactions occurring during reforming operation include dehydrogenation of cyclohexanes to aromatics, dehydroisomerization of alkylcyclopentanes to aromatics, dehydrocyclization of acyclic hydrocarbons to aromatics, dealkylation of alkylbenzenes, isomerization of paraffins, and hydrocracking reactions which produce light gaseous hydrocarbons, e.g., methane, ethane, propane and butanes. Hydrocracking reactions should be minimized during reforming as they decrease both the yield of products in the gasoline boiling range and the yield of the hydrogen.

Because of the demand for high octane gasoline for use in motor fuels, extensive research is being devoted to developing improved reforming catalysts and catalytic reforming processes. Catalysts for reforming processes must be able to produce high yields of liquid products in the gasoline boiling range and low yields of light gaseous hydrocarbons. The catalysts should possess good activity in order that low temperatures can produce a quality product. The catalysts should also either possess good stability, in order that the activity and selectivity characteristics can be retained during prolonged periods of operation, or be sufficiently regenerable to allow frequent regeneration without loss of performance.

Catalysts comprising platinum, for example, platinum and rhenium supported on chlorided alumina, are widely used for the reforming of naphthas.

In conventional reforming, the hydrocarbons to be converted are passed over the catalyst, in the presence of hydrogen, at temperatures of about 450° C. to 550° C. and pressures of about 50 to 500 psig. Part of the hydrocarbons are converted into aromatic hydrocarbons, and the reaction is accompanied by isomerization and cracking reactions which also convert the paraffins into isoparaffins and lighter hydrocarbons.

The conventional catalysts have given fairly satisfactory results with heavy paraffins, but less satisfactory results with $C_6$–$C_8$ paraffins, particularly $C_6$ paraffins. Catalysts based on a type L zeolite are more selective with regard to the dehydrocyclization reaction and produce excellent results with $C_6$–$C_8$ paraffins.

Still more selective for dehydrocyclization of $C_6$–$C_8$ paraffins are large-pore zeolitic catalysts that contain an alkaline earth metal and at least one Group VIII metal. Such zeolitic catalysts are disclosed in U.S. patent application Ser. No. 344,572 now U.S. Pat. No. 4,435,283.

SUMMARY OF THE INVENTION

The present invention increases the selectivity for dehydrocyclization of these Group VIII metal-alkaline earth metal large-pore zeolites by changing the way that the alkaline earth metal is added to the catalyst. In the present invention, the large-pore zeolite is doubly contacted with a solution containing the alkaline earth metal. Between the two contacting steps are a drying step and a calcination step.

Preferably, barium is added to a large-pore zeolite by contacting the large-pore zeolite with a barium nitrate solution at a pH of from 8 to 11, drying the contacted large-pore zeolite, calcining the dried large-pore zeolite at a temperature of from 500° C. to 700° C., and contacting the calcined large-pore zeolite with the barium nitrate solution at the same conditions as the first ion exchange step.

In one embodiment, a reforming catalyst is formed by ion exchanging a potassium-type L zeolite with a barium nitrate solution at a pH of from 9.5 to 10.2, drying the ion exchanged zeolite, calcining the dried zeolite at a temperature of from 580° C. to 600° C., ion exchanging the calcined zeolite with the barium nitrate solution at the same conditions as the first ion exchange step, drying and calcining the doubly exchanged zeolite, impregnating the doubly exchanged zeolite with platinum using tetrammineplatinum (II) nitrate, drying and calcining the impregnated zeolite, then reducing the calcined zeolite in hydrogen at 480° C. to 500° C.

DESCRIPTION OF THE PREFERRED EMBODIMENTS

In its broadest aspect, the present invention involves adding an alkaline earth metal to a large-pore zeolite by first contacting the zeolite with a solution containing an alkaline earth metal, then drying and calcining the contacted zeolite, and then contacting the calcined zeolite with the solution containing an alkaline earth metal.

Large-Pore Zeolite

The term "large-pore zeolite" is defined as a zeolite having an effective pore diameter of 6 to 15 Angstroms. Type L zeolite, zeolite X, and zeolite Y are thought to be the best large-pore zeolites for this operation and have apparent pore sizes of from 7 to 9 Angstroms.

The preferred large-pore zeolite is type L zeolite, which is described in detail in U.S. Pat. No. 3,216,789. Zeolite X is described in detail in U.S. Pat. No. 2,882,244. Zeolite Y is described in detail in U.S. Pat. No. 3,130,007. U.S. Pat. Nos. 3,216,789; 2,882,244; and 3,130,007 are hereby incorporated by reference to show large-pore zeolites useful in the present invention.

Alkaline Earth Metal

Two essential elements of the present invention are (1) the presence of an alkaline earth metal in the catalyst, and (2) the method by which the alkaline earth metal is added to the catalyst. That alkaline earth metal can be either barium, strontium or calcium. The preferred alkaline earth metal is barium because catalysts containing barium have high activity, high selectivity for dehydrocyclization, and high stability.

The presence of the alkaline earth metal in the catalyst is desired in order to achieve an exceptionally high selectivity for dehydrocyclization. The importance of having an alkaline earth metal present in the catalyst is shown in U.S. patent application Ser. No. 344,572, which is hereby incorporated by reference.

The alkaline earth metal is added to the large-pore zeolite by double ion exchange, with an intervening drying and calcination step. In the two ion exchange steps, the zeolite is contacted with a solution containing alkaline earth metal ions, preferably in excess of the zeolite exchange capacity. Preferably, the ion exchange occurs at a temperature of from 25° C. to 100° C., at a pH of from 8 to 11, and over a period of time of from 20 minutes to 4 hours. In a preferred embodiment, the large-pore zeolite is contacted with a barium nitrate solution. The barium should preferably constitute from 0.1% to 35% by weight of the final product, more preferably from 1% to 20% by weight.

In between the two ion exchange steps, the large-pore zeolite is dried and calcined. Preferably, the drying step occurs at a temperature of from 70° C. to 130° C., and the calcination step occurs at a temperature of from 550° C. to 650° C.

Group VIII Metals

The reforming catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrocyclization and are also more stable under the reforming reaction conditions than other Group VIII metals. The preferred percentage of platinum in the catalyst is between 0.1% and 5%, more preferably from 0.2% to 1.0%.

Group VIII metals are introduced into the zeolite during zeolite synthesis, or by subsequent impregnation or exchange using an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum (II) nitrate, tetrammineplatinum (II) hydroxide, dinitrodiamino-platinum or tetrammineplatinum (II) chloride. In an ion exchange process, platinum can be introduced by using cationic platinum complexes such as tetrammineplatinum (II) nitrate.

Catalyst Pellets

An inorganic oxide can be used as a carrier to bind the large pore size zeolite and to give the catalyst additional strength. The carrier can be a natural or a synthetically produced inorganic oxide or combination of inorganic oxides. The preferred percentage of inorganic oxide is from 5% to 50% by weight of the catalyst. Typical inorganic oxide supports which can be used include silica, alumina, and aluminosilicates.

It may be desirable to exchange the zeolite with the alkaline earth metal before binding the zeolite with a binder so that the catalyst is subjected to a minimum of exchangeable cations after it is bound.

In one embodiment, the zeolite is made, then the zeolite is ion exchanged with a barium solution, separated from the barium solution, dried and calcined, ion exchanged again with a barium solution, separated from the barium solution, dried and calcined, impregnated with platinum, dried, calcined, reduced in hydrogen at about 900° F., and then mixed with the inorganic oxide and extruded through a die to form cylindrical pellets, then the pellets are dried and calcined.

In another embodiment, the large-pore zeolite is mixed with the inorganic oxide and extruded through the die to form cyclindrical pellets, then the pellets are dried and calcined, then these pellets are ion exchanged with a barium solution, separated from the barium solution, dried, calcined, ion exchanged again with a barium solution, separated from the barium solution, dried, calcined, impregnated with platinum, separated from the platinum solution, dried and calcined, then reduced in hydrogen at about 900° F.

EXAMPLES

The invention will be further illustrated by the following examples which set forth particularly advantageous method and composition embodiments. While the examples are provided to illustrate the present invention, they are not intended to limit it.

EXAMPLE I

A first catalyst was prepared by (1) ion exchanging a potassium-type L zeolite with a sufficient volume of 0.17 molar barium nitrate solution to contain an excess of barium compared to the ion exchange capacity of the zeolite (no attempt was made to control pH); (2) drying the resulting barium-exchanged type L zeolite catalyst; (3) calcining the catalyst at 1100° F.; (4) impregnating the catalyst with 0.8% platinum using tetrammineplatinum (II) nitrate; (5) drying the catalyst at 150° F.; (6) calcining the catalyst at 500° F.; and (7) reducing the catalyst in hydrogen at 480° C. to 500° C.

EXAMPLE II

A second catalyst was prepared by (1) ion exchanging a potassium-type L at a pH of 10 with a sufficient volume of 0.17 molar barium nitrate solution to contain an excess of barium compared to the ion exchange capacity of the zeolite (pH was controlled with barium hydroxide); (2) drying the resulting barium-exchanged type L zeolite catalyst; (3) calcining the catalyst at 1100° F.; (4) ion exchanging the barium-exchanged type L zeolite catalyst with a sufficient volume of 0.17 molar barium nitrate solution to contain an excess of barium compared to the ion exchange capacity of the zeolite (pH was controlled to pH 10 with barium hydroxide); (5) drying the resulting barium-exchanged type L zeolite catalyst; (6) calcining the catalyst at 1100° F.; (7) impregnating the catalyst with 0.8% platinum using the tetrammineplatinum (II) nitrate; (8) drying the catalyst at 150° F.; (9) calcining the catalyst at 500° F. for 2 hours; and (10) reducing the catalyst in hydrogen at 480° C. to 500° C.

EXAMPLE III

The catalyst performance of these two catalysts was tested by using 0.5 gm of the catalysts to reform n-hexane, which had been hydrofined to remove sulfur, oxygen and nitrogen. The n-hexane was reformed at 890° F., 125 psi $H_2$, 4 ml (liquid)/hour n-hexane, 80 ml (gas)/minute hydrogen. At 20 hours on stream, the catalyst of Example I converted 35% of the n-hexane with 85% selectivity to benzene. At 20 hours on stream, the catalyst of Example II converted 33% n-hexane with 89% selectivity to benzene. Thus, using the catalyst of the present invention caused an increase of selectivity of 4% over that obtained by conventional ion exchange.

While the present invention has been described with reference to specific embodiments, this application is intended to cover those various changes and substitutions which may be made by those skilled in the art without departing from the spirit and scope of the appended claims.

What is claimed is:

1. A method of forming a zeolitic catalyst comprising:

(a) contacting a type L zeolite with a barium salt solution at a pH of from 8 to 11;
(b) drying said contacted type L zeolite at a temperature of from 70° C. to 130° C.;
(c) calcining said dried type L zeolite at a temperature of from 500° C. to 700° C.;
(d) contacting said calcined type L zeolite with said barium salt solution at a pH of from 8 to 11;
(e) drying and calcining said doubly contacted type L zeolite;
(f) impregnating the doubly contacted type L zeolite with a Group VIII metal; and
(g) drying and calcining the impregnated type L zeolite to form a zeolitic catalyst.

2. A method of forming a zeolitic catalyst according to claim 1 wherein said Group VIII metal is platinum.

3. A method of forming a zeolitic catalyst according to claim 2 wherein said final reforming catalyst has from 8% to 10% by weight barium and from 0.2% to 1.0% by weight platinum.

4. A method of forming a zeolitic catalyst according to claim 1 wherein said final reforming catalyst contains an inorganic binder.

5. A method of forming a zeolitic catalyst according to claim 4 wherein said inorganic binder is selected from the group consisting of silica, alumina, and aluminosilicates.

6. A method of forming a zeolitic catalyst comprising:
(a) contacting a potassium-type L zeolite with a barium nitrate solution at a temperature of from 25° C. to 100° C., at a pH of from 8 to 11, over a period of time of from 20 minutes to 4 hours;
(b) drying said contacted type L zeolite at a temperature of from 70° C. to 130° C.;
(c) calcining said dried type L zeolite at a temperature of from 550° C. to 650° C.;
(d) contacting said calcined type L zeolite with said barium nitrate solution at a temperature of from 25° C. to 100° C., at a pH of from 8 to 11, over a period of time of from 20 minutes to 4 hours;
(e) drying and calcining said doubly contacted type L zeolite;
(f) impregnating said doubly contacted type L zeolite with platinum using tetrammineplatinum (II) nitrate;
(g) drying and calcining said impregnated platinum-barium-type L zeolite;
(h) reducing said calcined platinum-barium-type L zeolite in hydrogen at 480° C. to 500° C.;
(i) mixing said reduced platinum-barium-type L zeolite with an inorganic binder selected from the group consisting of silica, alumina, and aluminosilicates;
(j) extruding said mixture through a die to form cylindrical pellets; and
(k) drying and calcining said pellets.

7. A method of forming a zeolitic catalyst comprising:
(a) mixing a potassium-type L zeolite with an inorganic binder selected from the group consisting of silica, alumina, and aluminosilicates;
(b) extruding said mixture through a die to form cylindrical pellets;
(c) drying and calcining said pellets;
(d) contacting said calcined pellets with a barium nitrate solution at a temperature of from 25° C. to 100° C., at a pH of from 8 to 11, over a period of time of from 20 minutes to 4 hours;
(e) drying said contacted pellets at a temperature of from 70° C. to 130° C.;
(f) calcining said dried barium-type L zeolite-inorganic oxide pellets at a temperature of from 550° C. to 650° C.;
(g) contacting said calcined barium-type L zeolite-inorganic oxide pellets with said barium nitrate solution at a temperature of from 25° C. to 100° C., at a pH of from 8 to 11, over a period of time of from 20 minutes to 4 hours;
(h) drying and calcining said doubly contacted pellets;
(i) impregnating said doubly contacted pellets with platinum using tetrammineplatinum (II) nitrate;
(j) drying and calcining said impregnated pellets; and
(k) reducing said calcined platinum-barium-type L zeolite-inorganic oxide pellets in hydrogen at 480° C. to 500° C.

8. A method of forming a zeolitic catalyst comprising:
(a) contacting a potassium-type L zeolite with a barium nitrate solution at a temperature of from 25° C. to 100° C., at a pH of from 8 to 11, over a period of time of from 20 minutes to 4 hours;
(b) drying said contacted type L zeolite at a temperature of from 70° C. to 130° C.;
(c) calcining said dried type L zeolite at a temperature of from 550° C. to 650° C.;
(d) contacting said calcined type L zeolite with said barium nitrate solution at a temperature of from 25° C. to 100° C., at a pH of from 8 to 11, over a period of time of from 20 minutes to 4 hours;
(e) drying and calcining said doubly contacted type L zeolite;
(f) mixing said doubly contacted type L zeolite with an inorganic binder selected from the group consisting of silica, alumina, and aluminosilicates;
(g) extruding said mixture through a die to form cylindrical pellets; and
(h) drying and calcining said pellets;
(i) impregnating said calcined pellets with platinum using tetrammineplatinum (II) nitrate;
(j) drying and calcining said impregnated pellets;
(k) reducing said calcined platinum-barium-type L zeolite-inorganic oxide pellets in hydrogen at 480° C. to 500° C.

* * * * *